United States Patent [19]

Rieber et al.

[11] Patent Number: 4,562,262
[45] Date of Patent: Dec. 31, 1985

[54] PREPARATION OF POLYCYCLIC NITROGEN-CONTAINING COMPOUNDS

[75] Inventors: Norbert Rieber, Mannheim; Heinrich Böhm, Neuhofen; Rolf Platz, Mannheim; Werner Fuchs, Ludwigshafen, all of Fed. Rep. of Germany

[73] Assignee: BASF Aktiengesellschaft, Fed. Rep. of Germany

[21] Appl. No.: 675,467

[22] Filed: Nov. 28, 1984

Related U.S. Application Data

[63] Continuation of Ser. No. 221,539, Dec. 31, 1980, abandoned.

[30] Foreign Application Priority Data

Jan. 17, 1980 [DE] Fed. Rep. of Germany ....... 3001580

[51] Int. Cl.$^4$ ........................................... C07D 487/04
[52] U.S. Cl. .................................................. 548/257
[58] Field of Search .......................................... 548/257

[56] References Cited

U.S. PATENT DOCUMENTS 4,189,434  2/1980  Platz et al. .......................... 548/257

FOREIGN PATENT DOCUMENTS 2615878  10/1977  Fed. Rep. of Germany ...... 548/257

OTHER PUBLICATIONS

Ohme, Preuschlof, Heyne; *Organic Synthesis*, vol. 52, pp. 11-15 (1972).
March, Jerry, *Advanced Organic Chemistry: Reactions, Mechanisms, and Structure*, Reaction 9-8.
Reiber, J. of Amer. Chem. Soc., 91:20, pp. 5668-5669, (1969).

*Primary Examiner*—Donald G. Daus
*Assistant Examiner*—G. Hendricks
*Attorney, Agent, or Firm*—Keil & Weinkauf

[57] ABSTRACT

A process for the preparation of polycyclic nitrogen-containing compounds of the formula

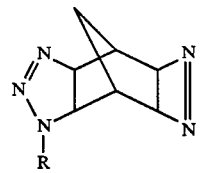

where R is hydrogen or an organic radical, wherein a compound of the formula

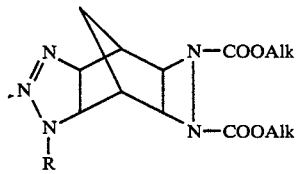

where Alk is alkyl of 1 to 4 carbon atoms and R has the above meanings, is reacted with a solution of an alkali metal hydroxide or of calcium hydroxide and the product is then oxidized.

8 Claims, No Drawings

PREPARATION OF POLYCYCLIC NITROGEN-CONTAINING COMPOUNDS

This application is a continuation of application Ser. No. 221,539, filed on Dec. 31, 1980, now abandoned.

The present invention relates to a process for the preparation of polycyclic nitrogen-containing compounds by reacting the corresponding dialkoxycarbonyl compounds with an alkali metal hydroxide or calcium hydroxide, and oxidizing the product.

German Laid-Open Application DOS No. 2,615,878 discloses polycyclic nitrogen-containing compounds, their preparation and use. The compounds include those of the formulae I and II

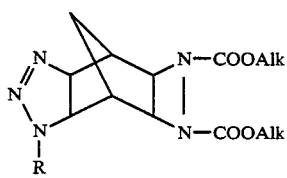

I

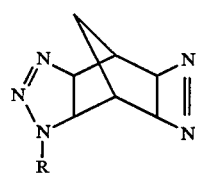

II where Alk is alkyl of 1 to 4 carbon atoms and R is hydrogen or is cyclic, acyclic, branched or unbranched alkyl, alkenyl or alkynyl of 1-30 carbon atoms, phenyl, naphthyl or a more highly condensed aromatic radical, a hetrocyclic radical containing one or more heteroatoms, (the hetero-atoms being O, N or S) or aralkyl in which the aromatic moiety may also be replaced by a heterocyclic ring, and the above radicals, other than hydrogen, may be monosubstituted or polysubstituted.

These compounds are prepared in a conventional manner, illustrated below, by reaction of an alkyl azide, aryl azide, aralkyl azide or heterocyclic azide, of the formula R—N₃, R having the above meanings, with a compound III or IV.

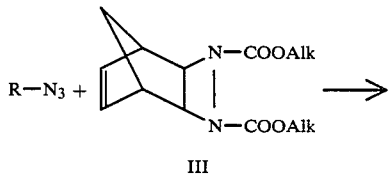

III

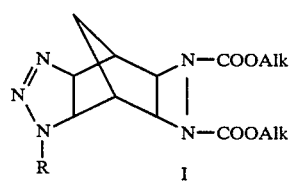

I

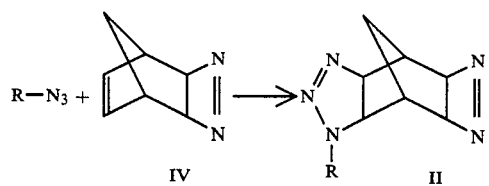

Compound IV is obtained, as described in J. Amer. Chem. Soc., 91 (1969), 5668, by hydrolyzing and decarboxylating a compound III, where Alk is CH₃, to give the hydrazine derivative, converting the hydrazine derivative to a Cu(I) complex of IV by means of CuCl₂, liberating IV with aqueous sodium hydroxide solution and extracting it from the sodium hydroxide phase by means of an organic solvent, the overall yield being 36%. This method of synthesis is illustrated below.

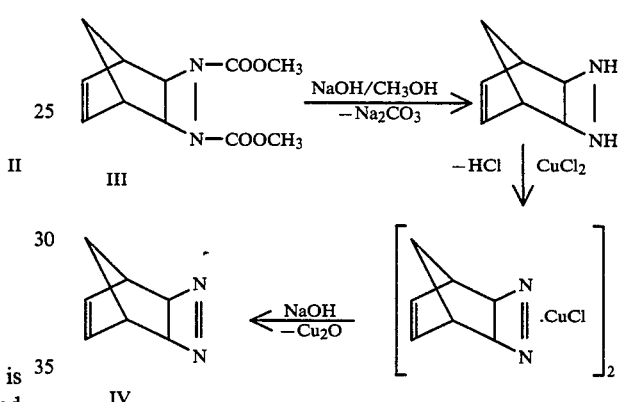

Compared to the synthesis of compounds I, the preparation of compounds II, by the sequence indicated above, is very expensive since, first, compound III has to be converted to compound IV by a method which uses an expensive compound, CuCl₂, necessitates isolating the copper complex and gives a yield of only 36%, and thereafter compound IV has to be reacted with R—N₃.

It is an object of the present invention to provide a simple and cheap process for preparing compounds II in high yields.

We have found that this object is achieved and that in the preparation of the compounds of the formula where R is hydrogen or is cyclic, acyclic, branched or unbranched alkyl, alkenyl or alkynyl of 1–30 carbon atoms, phenyl, naphthyl or a more highly condensed aromatic radical, a heterocyclic radical containing one or more hetero-atoms, (the hetero-atoms being O, N or S) or aralkyl in which the aromatic moiety may also be replaced by a heterocyclic ring, and the above radicals, other than hydrogen, may be monosubstituted or polysubstituted, a substantial improvement is attained if a compound of the formula

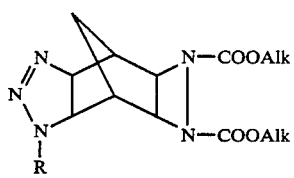

where R has the above meanings and Alk has the meaning given on page 1 is reacted with a solution of an alkali metal hydroxide or of calcium hydroxide and the product is then oxidized. A suitable alkali metal hydroxide is, for example, sodium hydroxide or potassium hydroxide or a mixture of these.

The process may, for example, be carried out as follows:

1. The azide R—N$_3$ is reacted with compound III to give compound I, as described in German Laid-Open Application DOS No. 2,615,878.

2. Compound I is converted in a simple manner, and in high yield, to compound II by hydrolysis, decarboxylation and oxidation without isolation of the individual intermediates, and without employing the expensive compound CuCl$_2$.

Specifically, the novel process is carried out, for example, by hydrolyzing and decarboxylating compound I with an aqueous or methanolic alkali metal hydroxide solution at 20°–100° C., preferably 40°–80° C., and oxidizng the hydrazine derivative formed as an intermediate, without isolation, by addition of aqueous NaOCl or H$_2$O$_2$ solution to the reaction mixture at 20°–100° C., preferably at 40°–80° C., to give a high yield of compound II.

This novel method of synthesis can be employed for all the compounds of type II, mentioned in German Laid-Open Application DOS No. 2,615,878, which have radicals R (referred to as R$^1$ in the DOS) which are stable to alkaline NaOCl solution or H$_2$O$_2$ solution.

The reaction of the compound III with the azide R—N$_3$ is carried out, for example, with an equimolar amount of the starting materials or with an excess of R—N$_3$.

The reaction of the compound I with a solution of an alkali metal hydroxide or of calcium hydroxide is carried out, for example, with solutions containing from 1 to 500 g of hydroxide, depending on its solubility, per liter of water or methanol, from 4 to 8 moles of hydroxide being employed per mole of compound I.

The oxidation is carried out with an aqueous solution of sodium hypochlorite or of hydrogen peroxide, containing from 1 to 500 g of oxidizing agent per liter of solution. From 1 to 10 moles of oxidizing agent are employed per mole of compound I.

The novel process is described below, for the case of the synthesis of the compound of the formula II, wherein R is p-chlorophenyl, in comparison with the conventional process.

According to German Laid-Open Application DOS No. 2,615,878 (Example 1), reaction of 92 parts by weight of p-chlorophenyl azide with 72 parts of compound IV gives 148 parts of compound II (wherein R is p-chlorophenyl), the yield being 90%.

To prepare 72 parts of compound IV by the method of synthesis described in German Laid-Open Application DOS No. 2,615,878 and in J. Amer. Chem. Soc. 91 (1969), 5668, 396 parts of compound III are required, the yield of compound IV being 36%.

If this same amount of compound is prepared by the process according to the invention, only 143 parts of compound III and 92 parts of p-chlorophenyl azide are required as starting materials. The reaction of the p-chlorophenyl azide with compound III to give compound I carried out as described in Example 2 of German Laid-Open Application DOS No. 2,615,878, gives a yield of 93%, and the conversion of compound I to compound II by the process according to the invention gives a yield of 97%.

EXAMPLE 1

339 parts of compound I (wherein R is p-chlorophenyl) are suspended in 1,110 parts of 25% strength by weight aqueous sodium hydroxide solution and the mixture is stirred for 6 hours at 85° C. 969 parts of 13% strength aqueous NaOCl solution are then added in the course of 2 hours at 60° C., and stirring is continued for a further 2 hours at the same temperature. When the mixture has cooled to 20° C., the solid product is filtered off, washed with 2,000–3,000 parts of water and dried.

230 parts (=97 mole %) of compound II (wherein R is p-chlorophenyl), melting, with decomposition, at 192° C., are obtained.

EXAMPLE 2

A solution of 123 parts of NaOH in 1,100 parts of methanol is added to a suspension of 300 parts of compound I (wherein R is p-chlorophenyl) in 1,000 parts of methanol in the course of 15 minutes at 68° C., whilst stirring. When all has been added, stirring is continued at the same temperature for 75 minutes, after which 260 parts of 30% strength aqueous H$_2$O$_2$ solution are added in the course of 15 minutes. The mixture is then stirred for a further hour at 68° C.

Thereafter, 1,600 parts of methanol are distilled off under reduced pressure, at a maximum temperature of the mixture of 65° C., and 2,000 parts of fully demineralized water are then added in the course of 15 minutes, whilst stirring.

The product which precipitates is filtered off, washed twice with 500 parts of fully demineralized water and dried.

199 parts of compound II (wherein R is p-chlorophenyl), melting, with decomposition, at 193° C., are obtained; the yield is about 95 mole %.

The other compounds of the formula II described in German Laid-Open Application DOS No. 2,615,878 may also be prepared by the process according to the invention.

We claim:

1. A process for the preparation of a polycyclic nitrogen-containing compound of the formula

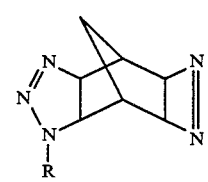

(II)

wherein R is phenyl, halo-substituted phenyl and CF$_3$-substituted phenyl which comprises reacting a compound of the formula

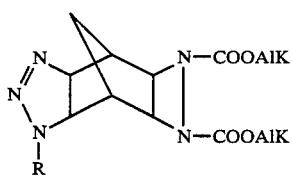 (I)

where R is defined as above and Alk is a $C_{1-4}$ alkyl with a solution of an alkali metal hydroxide or calcium hydroxide and then oxidizing the product with an aqueous solution of sodium hypochlorite or hydrogen peroxide.

2. The process of claim 1 wherein R is p-halophenyl.

3. The process of claim 1 wherein R is p-chlorophenyl.

4. The process of claim 1, wherein the reaction with the alkali metal hydroxide solution, and the oxidation, are carried out at from 20° to 100° C.

5. The process of claim 1, wherein the reaction with the alkali metal hydroxide solution and the oxidation are carried out successively, without isolating an intermediate compound.

6. The process of claim 1, wherein the starting material used for the process is a compound of the formula

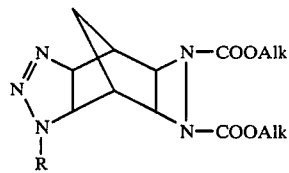

which has been prepared by reacting a compound of the formula

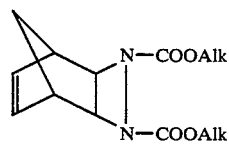

with an azide of the formula $R-N_3$, R and Alk having the meanings given in claim 1.

7. The process of claim 1 wherein 4 to 8 moles of hydroxide are used per mole of compound I.

8. The process of claim 1 wherein 1 to 10 moles of sodium hypochlorite or hydrogen peroxide are used per mole of compound I.

* * * * *